US011324902B1

(12) United States Patent
Esplin et al.

(10) Patent No.: US 11,324,902 B1
(45) Date of Patent: May 10, 2022

(54) OXYGEN DELIVERY PILLOW

(71) Applicants: Anthony Esplin, South Bend, IN (US); Aaron Esplin, Salt Lake City, UT (US)

(72) Inventors: Anthony Esplin, South Bend, IN (US); Aaron Esplin, Salt Lake City, UT (US)

(73) Assignee: Sleep Easy Technology LLC, South Bend, IN (US)

( * ) Notice: Subject to any disclaimer, the term of this patent is extended or adjusted under 35 U.S.C. 154(b) by 0 days.

(21) Appl. No.: 17/193,934

(22) Filed: Mar. 5, 2021

Related U.S. Application Data

(60) Provisional application No. 62/985,877, filed on Mar. 5, 2020.

(51) Int. Cl.
*A61M 16/00* (2006.01)
*A47G 9/10* (2006.01)

(52) U.S. Cl.
CPC ....... *A61M 16/0003* (2014.02); *A47G 9/1045* (2013.01); *A61M 2016/0027* (2013.01)

(58) Field of Classification Search
None
See application file for complete search history.

(56) References Cited

U.S. PATENT DOCUMENTS

| | | | | |
|---|---|---|---|---|
| 5,305,483 | A | * | 4/1994 | Watkins ............... A47D 15/001 128/202.18 |
| 2007/0006382 | A1 | * | 1/2007 | Guez ....................... A47G 9/10 5/638 |

FOREIGN PATENT DOCUMENTS

| | | | | | |
|---|---|---|---|---|---|
| CN | 209252279 | U | * | 8/2019 | |
| JP | 2006-367500 | | * | 5/2006 | |
| KR | 200419814 | | * | 6/2006 | |
| KR | 200419814 | Y1 | * | 6/2006 | |
| WO | WO-2018058906 | | * | 4/2018 | |
| WO | WO-2018058906 | A1 | * | 4/2018 | ............ A61M 16/00 |

* cited by examiner

Primary Examiner — Margaret M Luarca
(74) Attorney, Agent, or Firm — Dentons Durham Jones Pinegar

(57) ABSTRACT

An oxygen delivery pillow includes a shaped cushion, an oxygen delivery system, and a cover. The shaped cushion includes a top surface with a recess that can receive a subject's head. The oxygen delivery system delivers oxygen to the recess. When oxygen is delivered to the recess, it collects within an open space and then passes through the cover to a location around the subject's head on the cover and partially in the recess where it can be readily inhaled by the subject.

20 Claims, 3 Drawing Sheets

OXYGEN DELIVERY PILLOW

CROSS-REFERENCE TO RELATED APPLICATION

A claim for priority to the Mar. 5, 2020 filing date of U.S. Provisional Patent Application No. 62/985,877, titled OXYGEN DELIVERY PILLOW ("the '877 Provisional Application") is hereby made pursuant to 35 U.S.C. § 119(e). The entire disclosure of the '877 Provisional application is hereby incorporated herein.

TECHNICAL FIELD

This disclosure relates generally to devices for delivering oxygen to a subject while the subject sleeps and, more specifically, to pillows that deliver oxygen to a subject. More specifically, this disclosure relates to pillows that are connectable to oxygen delivery systems. Oxygen delivery systems that include a pillow that delivers oxygen to a subject are also disclosed, as are methods for delivering oxygen to a subject as the subject sleeps.

RELATED ART

A variety of health conditions may lead to the need for supplemental oxygen. Among other conditions, supplemental oxygen helps subjects who suffer from sleep apnea, acute bronchitis, asthma, heart conditions, chronic obstructive pulmonary disease (COPD), dementia, Alzheimer's, and other disorders achieve more stable, restful states of sleep than those subject's typically experience without supplemental oxygen. A variety of apparatuses, including conventional oxygen delivery systems, may be used to provide sleep apnea patients with supplemental oxygen as they sleep.

A conventional oxygen delivery system typically includes an oxygen concentrator or a continuous positive airway pressure (CPAP) machine, tubing, and a nasal cannula that delivers oxygen from the oxygen concentrator or CPAP machine to a subject's nose. The oxygen concentrator concentrates oxygen from the air, providing air with an above-ambient concentration of oxygen, which is also referred to herein as "supplemental oxygen" for the sake of simplicity. The oxygen concentrator delivers the supplemental oxygen to and through tubing to the nasal cannula. The nasal cannula has a configuration that enables it to be secured beneath a subject's nose in an orientation that directs the pressurized, supplemental oxygen into the subject's nose. It is up to the patient to breathe in to access that oxygen from the nasal cannula. If the patient is a mouth breather, as over 70% of people are when they sleep, the concentrated oxygen is not inhaled.

The use of nasal cannula can be uncomfortable and irritating. The presence of the nasal cannula beneath the subject's nose may be bothersome. In addition, the delivery of supplemental oxygen into a subject's nose has a tendency to dry out the subject's nasal membranes, which may make the nasal cannula even more bothersome. The discomfort a subject experiences while wearing a nasal cannula and while the nasal cannula delivers regulated, supplemental oxygen to the subject's nose may lead to removal of the nasal cannula—either intentionally or unintentionally—as the subject tries to sleep. When the nasal cannula is removed or the subject breathes through their mouth, however, the subject no longer receives supplemental oxygen, which may cause the same problem the supplemental oxygen is intended to address (e.g., fitful, interrupted sleep for sleep apnea patients, etc.).

DISCLOSURE

In various aspects, this disclosure relates to apparatuses, systems, and methods that may be used to provide a subject with supplemental oxygen.

In one aspect, an oxygen delivery pillow is disclosed. The oxygen delivery pillow may include a shaped cushion, a cover, and an oxygen transport conduit. The cover may be placed over the shaped cushion. The oxygen transport conduit may extend from an exterior of the cover, through portions of the cover and the shaped cushion, to an interior location where it can deliver supplemental oxygen between the shaped cushion and the cover.

The shaped cushion may include a recess for a subject's head. In a more specific embodiment, the recess may be defined in a top surface of the shaped cushion as a recessed area between two ends of the shaped cushion. A shape of the recess may enable it to accommodate a subject's head in a variety of orientations (e.g., a side of the subject's head as he or she lies on his or her side or chest, the subject's face as he or she lies on his or her chest, a back of the subject's head as he or she lays on his or her back, etc.).

In addition to including a recess for a subject's head, a shaped cushion of an oxygen delivery pillow according to this disclosure may include a channel that can receive at least a portion of the oxygen transport conduit. The channel enables the oxygen transport conduit to transport supplemental oxygen from a location outside of, or external to, the pillow to the recess of the shaped cushion. The channel may comprise a conduit through a portion of the shaped cushion or it may open to a surface of the shaped cushion.

In other embodiments, a shaped cushion may include a plurality of channels and a plurality of oxygen transport conduits carried by the plurality of channels and arranged in an oxygen delivery network. Such an embodiment may render the oxygen delivery system adjustable to enable oxygen to be delivered to any of a plurality of different locations in the recess of the shaped cushion. The ability to deliver oxygen to a plurality of different locations within the recess may accommodate a variety of different sleeping positions (e.g., subjects who might sleep differently on the pillow than a typical subject, etc.). Alternatively, embodiments of shaped cushions that include pluralities of channels and oxygen transport conduits may facilitate the distribution and simultaneous delivery of supplemental oxygen to a plurality of locations within the recess.

The oxygen transport conduit of the oxygen delivery pillow may include an exterior end, an intermediate portion, and an interior end. The exterior end may include a coupling element that can couple to a tube that extends from a source of the supplemental oxygen. The coupling element may comprise a standard nasal cannula connector. The intermediate portion may extend through a portion of the cover and a portion of the shaped cushion. The interior end may be positioned adjacent to or within the recess of the shaped cushion. Alternatively, in embodiments where the oxygen delivery pillow includes an oxygen distribution network, the interior end of the oxygen transport conduit may couple to a component of the oxygen distribution network, which may convey supplemental oxygen to the recess of the shaped cushion.

The cover may comprise a fabric. Air may be able to flow through the fabric, facilitating the flow of supplemental oxygen from the receptacle to a space within and above the receptacle, where the subject's the nose and/or mouth will be located as the subject's head is positioned on or in the recess. In some embodiments, the fabric may be permeable to air. In other embodiments, the fabric may include one or more ventilating features (e.g., an array of apertures, as in a mesh fabric; etc.). In addition to facilitating the communication of supplemental oxygen to a subject whose head rests on or in the recess of the shaped cushion, the cover may prevent soiling of the shaped cushion or otherwise protect the shape cushion (e.g., it may be impermeable to moisture, it may have antimicrobial properties, etc.).

In some embodiments, an oxygen delivery pillow according to this disclosure may also include a sensor that may be used to operate a source of supplemental oxygen. Such a sensor may detect the presence of a subject's head on the shaped cushion (e.g., a pressure sensor, etc.). The sensor may facilitate the flow of supplemental oxygen from its source to the oxygen delivery pillow (e.g., turn a source, such as an oxygen concentrator on; open a valve that enables supplemental oxygen to flow through the oxygen transport conduit; etc.) when a subject's head rests on the oxygen delivery pillow. When the subject's head is removed from the pillow, the sensor may terminate the flow of supplemental oxygen to the oxygen delivery pillow (e.g., by turning the source off; by closing a valve associated with the oxygen transport conduit; etc.).

In another aspect, this disclosure relates to oxygen delivery systems. An oxygen delivery system according to this disclosure includes a source of supplemental oxygen, tubing, and an oxygen delivery pillow. The source of supplemental oxygen may comprise an oxygen concentrator, a container carrying compressed oxygen, a container carrying liquid oxygen and an associated delivery apparatus, or the like. The tubing may comprise a conduit with a receiving end that couples to the source and a delivery end that couples to the oxygen delivery pillow to convey supplemental oxygen from the source to the oxygen delivery pillow. Some embodiments of oxygen delivery systems may also include components (e.g., a tent, etc.) that facilitates the collection of oxygen over the oxygen delivery pillow.

Methods for delivering oxygen to a subject are also disclosed. Such a method may include establishing flow communication between an oxygen delivery pillow and a source of supplemental oxygen (e.g., an oxygen concentrator, a container carrying compressed oxygen, a delivery apparatus for liquid oxygen, etc.), placing a subject's head on the oxygen delivery pillow at a location and in an orientation that will enable the subject to receive supplemental oxygen, and establishing the flow of supplemental oxygen from the source to the oxygen delivery pillow and, thus, to the subject. Flow communication may be established by coupling an oxygen transport conduit of the oxygen delivery pillow to the source (e.g., by way of tubing, etc.). Placement of the subject's head may include placing the subject's head over a recess in a shaped cushion of the oxygen delivery pillow, to which recess the supplemental oxygen will be delivered as the supplemental oxygen flows from the source to the oxygen delivery pillow.

Other aspects of this disclosure, as well as features and advantages of various aspects of this disclosure, should be apparent to those of ordinary skill in the art through consideration of the ensuing description, the accompanying drawings, and the appended claims.

DETAILED DESCRIPTION

Figure 1:
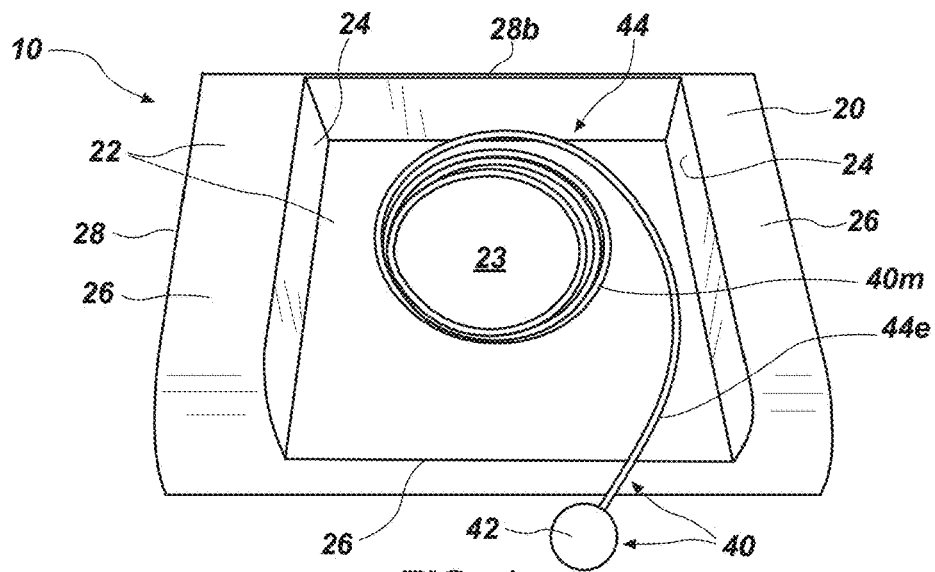
FIG. 1 illustrates a top surface of a shaped cushion of an embodiment of an oxygen delivery pillow according to this disclosure, showing raised edges and a receptacle in a top surface of the oxygen delivery pillow.

FIG. 1 depicts an embodiment of an oxygen delivery pillow 10 according to this disclosure. The oxygen delivery pillow 10 includes a shaped cushion 20 and an oxygen delivery system 40.

The shaped cushion 20 of the oxygen delivery pillow 10 includes a top surface 22, a bottom surface (not shown in FIG. 1), and an outer periphery 28. The top surface 22 includes a recess 23 at its center. The recess 23 includes an edge 24 extend along its sides and its top edge. The recess 23 opens to a base edge 28b of the outer periphery 28 of the shaped cushion 20. A raised area 26 is located between a remainder of the outer periphery 28 and the edge 24 of the recess 23. In some embodiments, a shape of the recess 23 may enable it to receive an individual's head (e.g., a side of the individual's head, the individual's face, etc.).

The recess 23 may have a configuration that enables it to receive a subject's head at an elevation where supplemental oxygen may collect and/or be directed toward the subject's face (e.g., from a side of the recess 23, from the bottom of the recess 23, at a location near an edge 24 of the recess 23, etc.).

Figure 2:
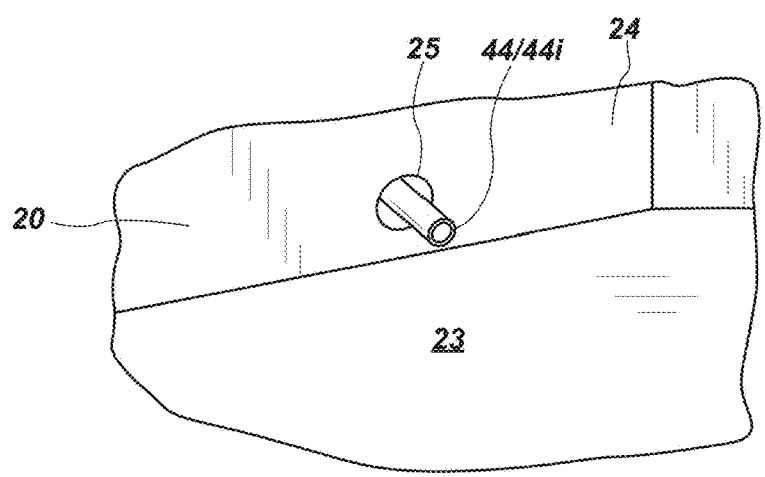
FIG. 2 provides a detailed view of an oxygen delivery port associated with the recess in the top of the embodiment of oxygen delivery pillow shown in FIG. 1.
Figure 3:
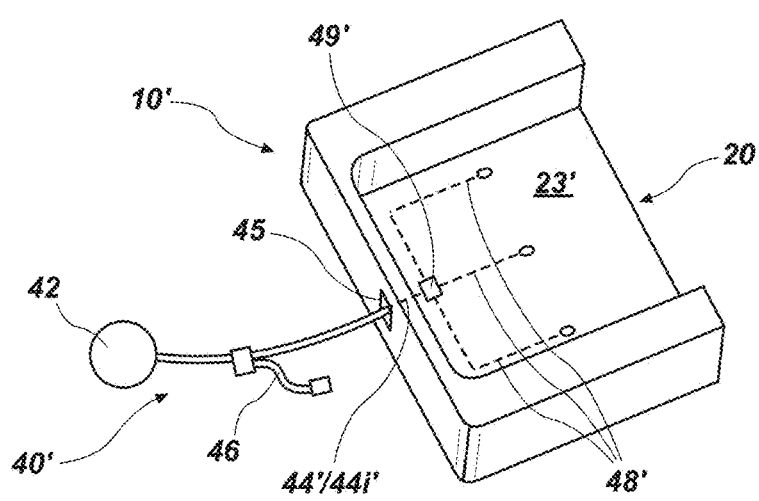
FIG. 3 illustrates a top surface of a shaped cushion of another embodiment of an oxygen delivery pillow according to this disclosure, in which showing raised edges and a receptacle in a top surface of the oxygen delivery pillow.

With added reference to FIG. 2, in addition to including the recess 23, the shaped cushion 20 may include a channel 25 that can receive at least a portion of an oxygen transport conduit 44 of the oxygen delivery system 40 (FIGS. 1 and 3). The channel 25 enables the oxygen transport conduit 44 to transport supplemental oxygen from a location outside of, or external to, the oxygen delivery pillow 10 to the recess 23. As depicted by FIG. 2, the channel 25 may open to an edge 24 of the recess 23.

The shaped cushion 20 may comprise any suitable cushioning material. In some embodiments, the shaped cushion 20 may comprise a shaped foam. Examples of foams that may be used to form the shaped cushion 20 include, but are not limited to, foam rubber (i.e., elastomeric foam), so-called memory foams (i.e., visco-elastic foams) (e.g., a gel memory foam, etc.) and the like. The shaped cushion 20 may be molded and/or sculpted.

The oxygen delivery system 40 may include a source 42 of oxygen and an oxygen transport conduit 44 for transporting oxygen from the source 42 to the recess 23. In some embodiments, the source 42 may comprise an oxygen concentrator of a known type. In other embodiments, the source 42 may comprise a container carrying compressed oxygen, a container carrying liquid oxygen and an associated delivery apparatus, or any other source of oxygen. The oxygen transport conduit 44 may comprise a tube with an exterior end 44e, an intermediate portion 44m, and an interior end 44i. The exterior end 44e may include a coupling element 45 (FIG. 3) that can couple to a tube that extends from source 42. The coupling element 45 may, without limitation, comprise a standard nasal cannula connector. The intermediate portion 44m of the oxygen transport conduit 44 may extend through a portion of the cover (60—FIGS. 4-7) and a portion of the shaped cushion 20. The interior end 44i of the oxygen transport conduit 44 may be positioned adjacent to or within the recess 23 of the shaped cushion 20, as shown in FIG. 2.

Alternatively, as illustrated by FIG. 3, in embodiments where an oxygen delivery pillow 10' includes an oxygen delivery system 40' with an oxygen distribution network 48' within the shaped cushion 20', the interior end 44i' of the oxygen transport conduit 44' may couple to a component of the distribution network 48', which may in turn convey supplemental oxygen to the recess 23' of the shaped cushion 20'. The oxygen distribution network 48' may include a plurality of interconnected conduits that can deliver oxygen to any of a plurality of different locations in the recess 23'. The plurality of interconnected conduits may comprise a distributor (e.g., a branched member, a reservoir or bladder, etc.) and a plurality of conduits in or carried by the shaped cushion that receive supplemental oxygen from the distributor and distribute it to a plurality of different locations in the recess 23'. In some embodiments, a valve 49' may provide for selective control over the location(s) of the oxygen distribution network 48' and, thus, locations within the recess 23' to which oxygen is delivered.

In some embodiments, the oxygen transport conduit 44, 44' may include a branch 46' to which a nasal cannula (not shown) may be selectively coupled.

Turning now to FIGS. 4-7, an embodiment of a cover 60 of an oxygen delivery pillow 10 (or oxygen delivery pillow 10', shown in FIG. 3) according to this disclosure is depicted. The cover 60 is designed to be placed over a shaped cushion (e.g., the shaped cushion 20 shown in FIG. 1, the shaped cushion 20' shown in FIG. 3, etc.). In some embodiments, the cover 60 may have a shape that enables it to form fit over the shaped cushion 20. A shape of the cover 60 may also provide for a space 70 (FIGS. 8 and 9), or gap, between the cover 60 and a surface of the recess 23 in the top surface 22 (FIG. 1) of the shaped cushion 20 over which the cover 60 is placed.

The cover 60 may comprise a fabric 62. A pliability of the fabric 62 may enable it to at least partially give as a subject's head is placed on the cover 60 at a location over a recess of the shaped cushion (e.g., the recess 23 of the shaped cushion 20 shown in FIG. 1, the recess 23' of the shaped cushion 20' shown in FIG. 3, etc.), which may enable the subject's head to be partially received by the recess.

Air may be able to flow through the fabric 62, facilitating the flow of supplemental oxygen from a recess of the shaped cushion (e.g., the recess 23 shown in FIG. 1, the recess 23' shown in FIG. 3, etc.) to a space within and above the recess, where the subject's the nose and/or mouth will be located as the subject's head is positioned over the recess and is at least partially received thereby. In some embodiments, the fabric 62 may be permeable to air. In other embodiments, the fabric 62 may include one or more ventilating features (e.g., an array of apertures, as in a mesh fabric; etc.).

In addition to facilitating the communication of supplemental oxygen to a subject whose head rests on or in the recess of the shaped cushion, the cover 60 may prevent soiling of the shaped cushion or otherwise protect the shape cushion (e.g., it may be impermeable to moisture, it may have antimicrobial properties, etc.).

Figure 4:
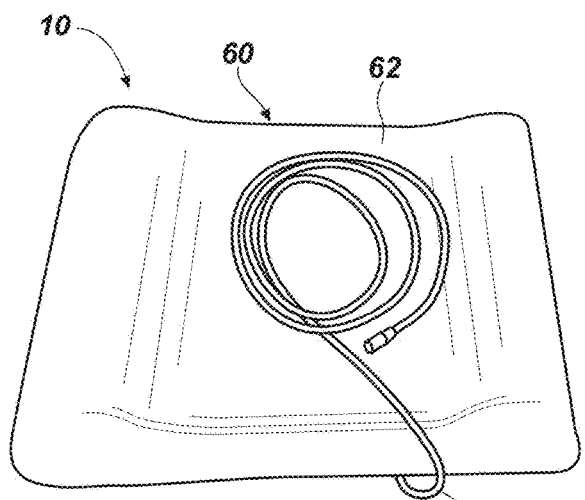
FIGS. 4 and 5 depict a bottom of a cover of the embodiments of oxygen delivery pillow shown in FIGS. 1 and 2, over the shaped cushion of the oxygen delivery pillow.
Figure 5:
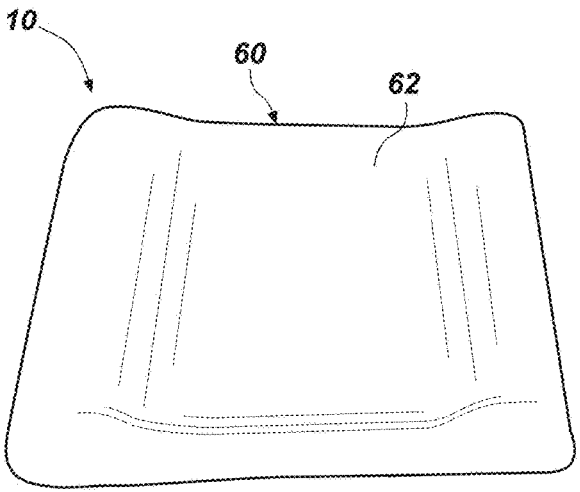
Figure 6:
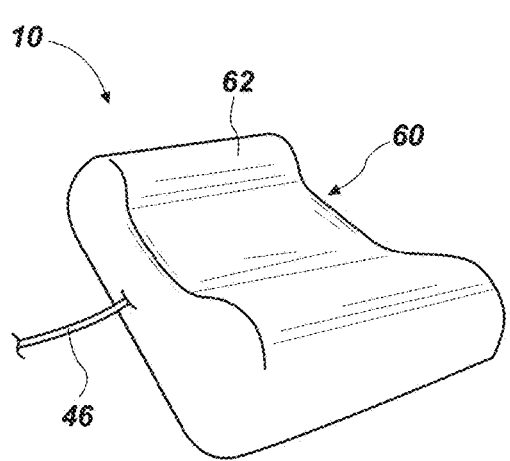
FIGS. 6 and 7 depict a top of the cover shown in FIGS. 4 and 5.
Figure 7:
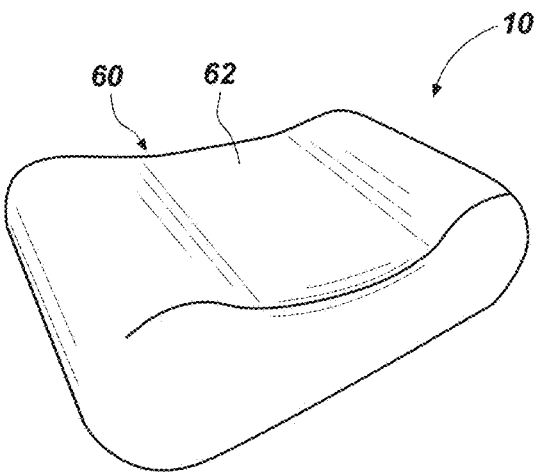

As depicted by FIGS. 4 and 6, the oxygen transport conduit 44 may extend into a bottom edge 64 of the cover 60, through a portion of the shaped cushion, and open to the recess in the shaped cushion.

Figure 8:
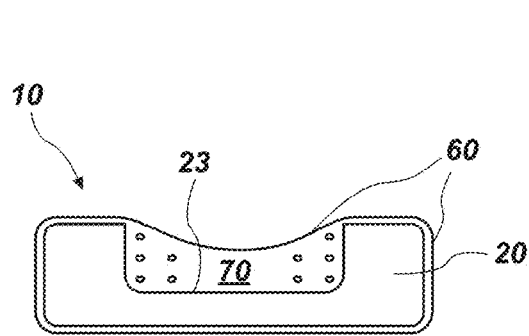
FIGS. 8 and 9 are, respectively, cross-sectional and top representations of the manner in which oxygen that has been delivered to the recess of the shaped cushion collects in the recess of the shaped cushion.
Figure 9:
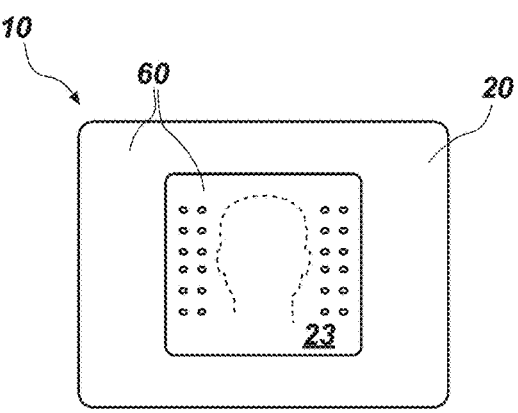

Referring now to FIGS. 8 and 9, the manner in which oxygen fills the recess 23 of a shaped cushion 20 of an oxygen delivery pillow 10 according to this disclosure is depicted. Oxygen behaves as a liquid in that it takes the path of least resistance. Accordingly, when supplemental oxygen is delivered to the recess 23 of shaped cushion 20 with a cover 60 thereover, it will fill a space 70 within the recess 23, beneath the cover 60 before passing through the cover 60. When a subject's head rests on the cover 60 over the recess 23, the supplemental oxygen will then pass through the cover 60 at one or more locations over the recess 23, where it can be readily inhaled by the subject.

Testing of the embodiment of oxygen delivery pillow 10 depicted by FIGS. 1, 2, and 4-7 using a mannequin head having a weight of about ten pounds revealed that when supplemental oxygen is delivered at a rate of about 10 L/min, the oxygen delivery pillow was able to deliver a fraction of inspired oxygen ($FiO_2$) at a rate of 5 L/min, which is equivalent to the delivery of supplemental oxygen at a rate of 2 L/min through a nasal cannula.

The oxygen delivery pillow 10 was tested with a five-year-old Down Syndrome child who has sleep apnea. He is supposed to wear a nasal cannula in the evening but refuses the wear it while he sleeps. The oxygen delivery pillow 10 allows supplemental oxygen to flow to the child's face without the need for him to wear a nasal cannula.

Figure 11:
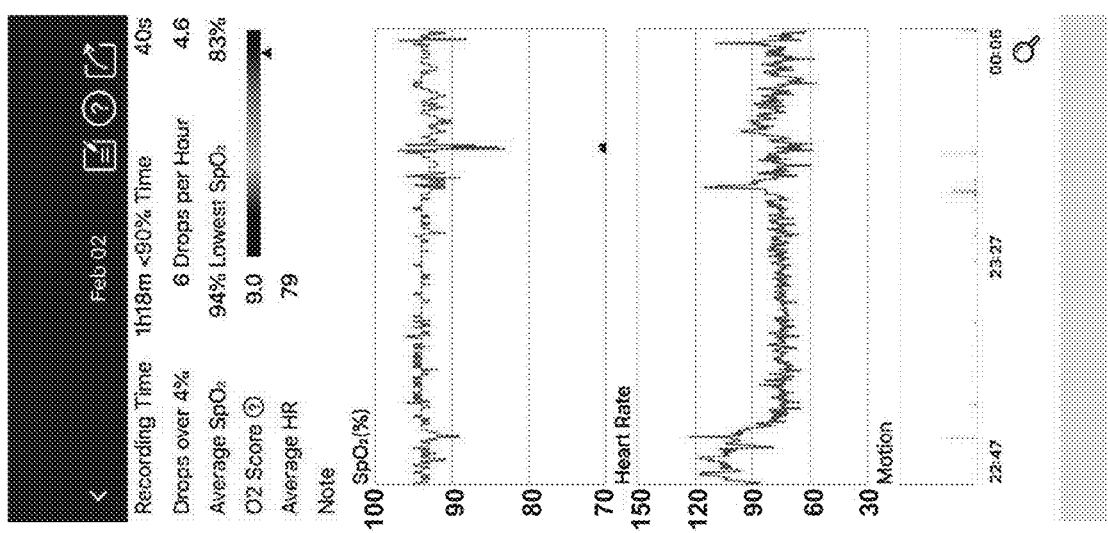
FIGS. 10 and 11 are charts showing the peripheral capillary blood oxygenation ($SpO_2$) of the subject on two evenings when he slept with a nasal cannula, which the subject removed both evenings.
Figure 10:
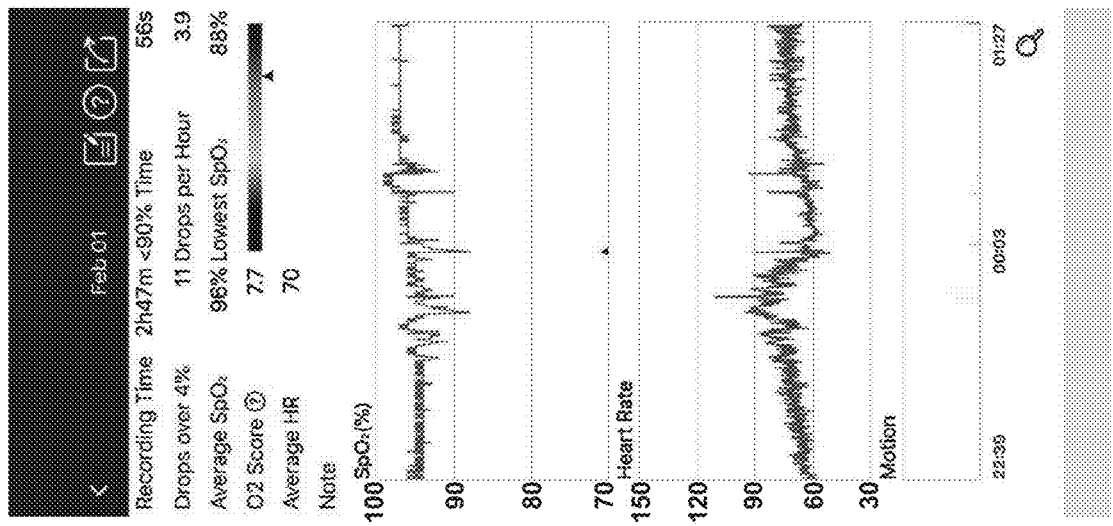

The charts of FIGS. 10 and 11 show the peripheral capillary blood oxygenation ($SpO_2$) of the subject on two evenings when he was put to bed with a nasal cannula, which was removed both evenings. Notably, the subject experienced significant drops in $SpO_2$ levels both evenings. A drop in $SpO_2$ of at least 3% represents an oxygen desaturation event. The number of oxygen desaturation events each hour is referred to as the oxygen desaturation index (ODI). The subject's ODI on the first evening was 3.9. His ODI the second evening was 4.6.

Figure 12:
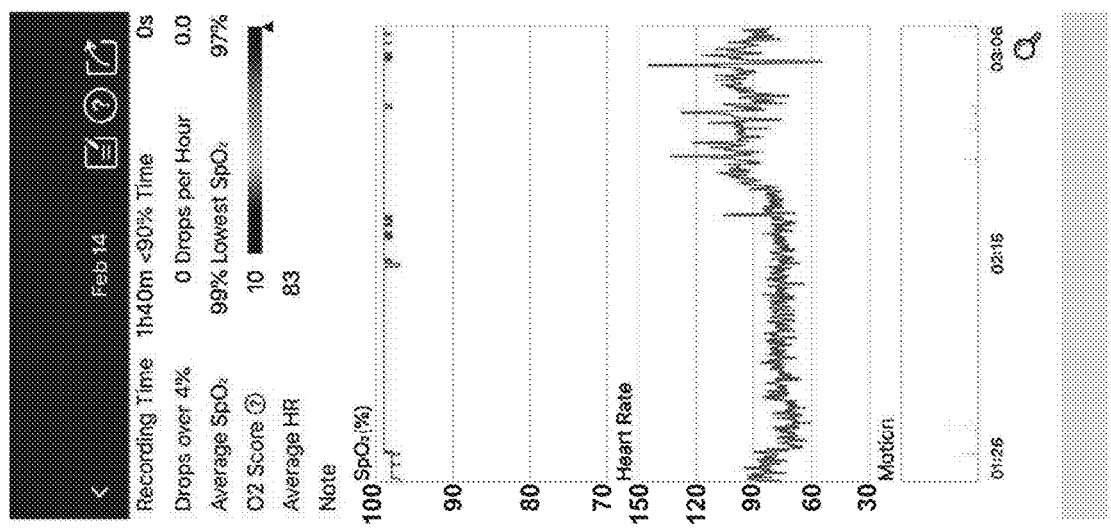
FIG. 12 is a chart showing the peripheral capillary blood oxygenation ($SpO_2$) of the subject on a third evening when he slept with the embodiment of oxygen delivery pillow shown in FIGS. 1-7.

The chart of FIG. 12 illustrates the effect replacement of the nasal cannula with the oxygen delivery pillow 10 had on the subject's sleep over the course of one evening. As the $SpO_2$ graph near the top of the chart shows, the subject did not experience any oxygen desaturation events when he slept with his head on the oxygen delivery pillow. Thus, his ODI for the evening was zero. It is also noteworthy that his average $SpO_2$ for the evening was 99%, as compared with significantly lower averages of 96% and 94% on evenings where he slept with and removed the nasal cannula. These data demonstrate that the oxygen delivery pillow 10 can effectively deliver oxygen to a subject while maintaining optimal $SpO_2$ levels while the subject sleeps.

Although this disclosure and the accompanying drawings provide many specifics, these should not be construed as limiting the scopes of any of the appended claims, but merely as providing information pertinent to some specific embodiments that may fall within the scopes of the appended claims. Features from different embodiments may be employed in combination. In addition, the scopes of the appended claims may encompass other embodiments. All additions to, deletions from, and modifications of the disclosed subject matter that fall within the scopes of the claims are to be embraced by the claims.

What is claimed:

1. An oxygen delivery system, comprising:
   a source of supplemental oxygen;
   an oxygen delivery pillow, comprising:
      a cushion including a portion that is permeable to air, the cushion including a recess that can accommodate a side of a head of a subject;
      a cover over the cushion;
      a channel extending through the cushion of the oxygen delivery pillow and defining an opening in a side wall of the recess; and
      an oxygen transport conduit extending from a location outside of the cushion to a location within the cushion, the oxygen transport conduit being at least partially positioned within the channel and extending substantially to or through the opening in the side wall of the recess, with an end of the oxygen transport conduit configured to deliver a directed flow of supplemental oxygen from the opening to a side of the recess toward a center of the recess; and
   a tube extending from the source to the oxygen transport conduit of the oxygen delivery pillow to enable communication of supplemental oxygen from the source to the oxygen delivery pillow.

2. The oxygen delivery system of claim 1, wherein the source of supplemental oxygen comprises an oxygen concentrator or an oxygen tank.

3. The oxygen delivery system of claim 1, wherein the cushion of the oxygen delivery pillow comprises a shaped cushion.

4. The oxygen delivery system of claim 1, wherein the oxygen transport conduit of the oxygen delivery pillow causes a flow of the supplemental oxygen to be directed into the recess through the side wall of the recess.

5. The oxygen delivery system of claim 4, wherein the oxygen transport conduit of the oxygen delivery pillow causes the flow of the supplemental oxygen to be directed from the side wall of the recess toward a face of the subject.

6. The oxygen delivery system of claim 1, wherein the oxygen delivery pillow further comprises:
   a distribution network that receives the supplemental oxygen from the oxygen transport conduit and conveys the supplemental oxygen to a plurality of locations on a surface of the cushion.

7. The oxygen delivery system of claim 1, wherein the oxygen delivery pillow further comprises:
   a pressure sensor that activates the source of supplemental oxygen.

8. The oxygen delivery system of claim 1, wherein the cover enables supplemental oxygen to flow from the cushion to a location above the oxygen delivery pillow.

9. The oxygen delivery system of claim 1, wherein the oxygen transport conduit is part of an oxygen distribution network that includes plurality of conduits that open to a plurality of locations within the recess of the cushion.

10. The oxygen delivery system of claim 9, wherein the oxygen distribution network further includes a valve that provides for selective control over a conduit of the plurality of conduits of the oxygen distribution network through which oxygen flows and a location of the plurality of locations within the recess of the cushion from which oxygen is delivered.

11. An oxygen delivery pillow, comprising:
   a cushion including a recess;
   a cover over the cushion and including a portion that is permeable to air;
   a channel formed in the cushion and defining an opening in a side of the recess of the cushion; and
   an oxygen transport conduit extending from a location outside of the cushion to a location within the cushion, the oxygen transport conduit being at least partially carried by the channel and extending substantially to or through the opening in the side of the recess and being configured to deliver a flow of air to the side of the recess, laterally toward a center of the cushion and the cover and toward a face of a subject whose head rests on the cover and the cushion.

12. The oxygen delivery pillow of claim 11, wherein the cushion comprises a shaped cushion.

13. The oxygen delivery pillow of claim 11, wherein the shaped cushion includes a recess that receives a subject's head.

14. The oxygen delivery system of claim 13, wherein the oxygen transport conduit delivers a flow of the supplemental oxygen to the side of the recess of the cushion.

15. The oxygen delivery pillow of claim 13, wherein the recess can accommodate a side of the subject's head.

16. The oxygen delivery pillow of claim 11, further comprising:
   a distribution network that receives the supplemental oxygen from the oxygen transport conduit and conveys the supplemental oxygen to a plurality of locations on a surface of the cushion.

17. The oxygen delivery pillow of claim 11, further comprising:
   a pressure sensor.

18. A method for delivering oxygen to a subject, comprising:
   establishing flow communication between an oxygen delivery pillow and a source of supplemental oxygen;
   placing a head of a subject at least partially in a recess of the oxygen delivery pillow at a location and in an orientation that will enable the subject to receive the supplemental oxygen; and
   establishing a flow of the supplemental oxygen from the source to the oxygen delivery pillow and to direct a flow of the supplemental oxygen through a conduit extending through an opening in a side of the recess of the oxygen delivery pillow and into a side of the recess, toward a face of the subject.

19. The method of claim 18, wherein establishing flow communication comprises establishing flow communication between the oxygen delivery pillow and an oxygen concentrator or an oxygen tank.

20. The method of claim 16, wherein establishing the flow of supplemental oxygen comprises causing the supplemental oxygen to flow from the side of a recess that receives the head of the subject.

* * * * *